US008187874B2

(12) United States Patent
Perni et al.

(10) Patent No.: US 8,187,874 B2
(45) Date of Patent: May 29, 2012

(54) DRUG DISCOVERY METHOD

(75) Inventors: Robert B. Perni, Marlborough, MA (US); Cynthia Gates, Princeton, NJ (US); John Thomson, Acton, MA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 41 days.

(21) Appl. No.: 10/975,196

(22) Filed: Oct. 27, 2004

(65) Prior Publication Data

US 2006/0003317 A1 Jan. 5, 2006

Related U.S. Application Data

(60) Provisional application No. 60/515,009, filed on Oct. 27, 2003, provisional application No. 60/526,346, filed on Dec. 1, 2003.

(51) Int. Cl.
*C12N 5/00* (2006.01)
(52) U.S. Cl. ..................... 435/339; 424/218.1
(58) Field of Classification Search ........................ None
See application file for complete search history.

(56) References Cited

U.S. PATENT DOCUMENTS

| 5,807,876 | A | 9/1998 | Armistead et al. |
| 5,866,684 | A | 2/1999 | Attwood et al. |
| 5,990,276 | A | 11/1999 | Zhang et al. |
| 6,018,020 | A | 1/2000 | Attwood et al. |
| 6,162,613 | A | 12/2000 | Su et al. |
| 2002/0016294 | A1 | 2/2002 | Venkatraman et al. |
| 2002/0016442 | A1 | 2/2002 | Llinas-Brunet et al. |
| 2002/0177725 | A1 | 11/2002 | Priestley |
| 2003/0008828 | A1 | 1/2003 | Priestley et al. |

FOREIGN PATENT DOCUMENTS

| WO | WO 95/30642 A1 | 11/1995 |
| WO | WO 95/32184 A1 | 11/1995 |
| WO | WO 95/35278 A1 | 12/1995 |
| WO | WO 97/43310 A1 | 11/1997 |
| WO | WO 98/11134 A1 | 3/1998 |
| WO | WO 98/17679 A1 | 4/1998 |
| WO | WO 98/22496 A3 | 5/1998 |
| WO | WO 98/46630 A1 | 10/1998 |
| WO | WO 99/07733 A3 | 2/1999 |
| WO | WO 99/07734 A3 | 2/1999 |
| WO | WO 99/38888 A3 | 8/1999 |
| WO | WO 99/50230 A1 | 10/1999 |
| WO | WO 99/64442 A1 | 12/1999 |
| WO | WO 00/09543 A3 | 2/2000 |
| WO | WO 00/09558 A1 | 2/2000 |
| WO | WO 00/09588 A1 | 2/2000 |
| WO | WO 00/31129 A1 | 6/2000 |
| WO | WO 00/59929 A1 | 10/2000 |
| WO | WO 01/07407 A1 | 2/2001 |
| WO | WO 01/64678 A3 | 9/2001 |
| WO | WO 01/74768 A3 | 10/2001 |
| WO | WO 01/77113 A3 | 10/2001 |
| WO | WO 01/81325 A3 | 11/2001 |
| WO | WO 02/08187 A1 | 1/2002 |
| WO | WO 02/08198 A3 | 1/2002 |
| WO | WO 02/08244 A3 | 1/2002 |
| WO | WO 02/08256 A3 | 1/2002 |
| WO | WO 02/18369 A3 | 3/2002 |
| WO | WO 02/48116 A2 | 6/2002 |
| WO | WO 02/48157 A3 | 6/2002 |
| WO | WO 02/060926 A3 | 8/2002 |
| WO | WO 02/068933 A2 | 9/2002 |
| WO | WO 02/079234 A1 | 10/2002 |
| WO | WO 03/006490 A1 | 1/2003 |
| WO | WO 03/035060 A1 | 5/2003 |
| WO | WO 03/064416 A1 | 8/2003 |
| WO | WO 03/064456 A1 | 8/2003 |
| WO | WO 03/087092 A3 | 10/2003 |

OTHER PUBLICATIONS

Lee et al. Analytical Biochemistry, 2003, vol. 316, p. 162-170.*
Kwong et al. Antiviral Research, 1999, vol. 41, p. 67-84.*
(Perni et al. Antimicrobial Agents and Chemotherapy, 2006, vol. 50, p. 899-909 in IDS on Jun. 4, 2010).*
Le Pogam et al. (Journal of Antimicrobial Therapy, 2008, vol. 61, p. 1205-1216).*
Alberti et al., J. Hepatol., 31 Suppl 1:17-24 (1999).
Alter et al., Gastroenterol. Clin. North Am., 23(3):437-455 (1994).
Alter, J. Hepatol., 31 Suppl 1:88-91 (1999).
Bartenschlager et al., J. Virol., 67(7):3835-3844 (1993).
Chambers et al., Proc. Natl. Acad. Sci. USA, 87:8898-8902 (1990).
Choo et al., Proc. Natl. Acad. Sci. USA, 88:2451-2455 (1991).
DeWitt et al., Proc. Natl. Acad. Sci. USA, 90:6909-6913 (1993).
Dunsdon et al., Bioorg. Med. Chem. Lett., 10:1577-1579 (2000).
Grakoui et al., J. Virol., 67(3):1385-1395 (1993).
Grakoui et al., J. Virol., 67(5):2832-2843 (1993).
Han et al., Bioorg. Med. Chem. Lett., 10:711-713 (2000).
Iwarson, FEMS Microbiol. Rev., 14:201-204 (1994).
J. Viral Hepat., 6:35-47 (1999).
Janssen et al., J. Hepatol., 21:241-243 (1994).
Kato et al., Proc. Natl. Acad. Sci. USA, 87:9524-9528 (1990).
Kew, FEMS Microbiol. Rev., 14:211-220 (1994).
Landro et al., Biochemistry, 36:9340-9348 (1997).
Lin et al., J. Virol., 68(12):8147-8157 (1994).
Llinas-Brunet et al., Bioorg. Med. Chem. Lett., 8:1713-1718 (1998).
Llinas-Brunet et al., Bioorg. Med. Chem. Lett., 10:2267-2270 (2000).
Moradpour et al., Eur. J. Gastroenterol. Hepatol., 11:1199-1202 (1999).
Morrison et al., Adv. Enzymol. Relat. Areas Mol. Biol., 61:201-301 (1988).
Morrison, Biochim. Biophys. Acta, 185:269-286 (1969).
Narjes et al., Biochemistry, 39:1849-1861 (2000).
Neumann et al., Science, 282:103-107 (1998).
Nowak et al., Proc. Natl. Acad. Sci. USA, 93:4398-4402 (1996).

(Continued)

*Primary Examiner* — Agnieszka Boesen
(74) *Attorney, Agent, or Firm* — Marshall, Gerstein & Borun LLP

(57) ABSTRACT

The present invention relates to drug discovery methods, particularly antiviral drug discovery methods.

16 Claims, 1 Drawing Sheet

OTHER PUBLICATIONS

Perelson et al., Science, 271:1582-1586 (1996).
Renault et al., Semin. Liver Dis., 9(4):273-277 (1989).
Saito et al., Proc. Natl. Acad. Sci. USA, 87:6547-6549 (1990).
Sculley et al., Biochim. Biophys. Acta, 1298:78-86 (1996).
Takamizawa et al., J. Virol., 65(3):1105-1113 (1991).
Tomei et al., J. Virol., 67(7):4017-4026 (1993).
Walker, Drug Discovery Today, 4(11):518-529 (1999).
Weiland, FEMS Microbiol. Rev., 14:279-288 (1994).
Jung et al., Angew. Chem. Int. Ed. Engl., 31:367-383 (1992).
Dash et al. "Slow-Tight Binding Inhibition of Xylanase by an Aspartic Protease Inhibitor," *The Journal of Biological Chemistry*, 277(20):17978-17986 (May 17, 2002).
Invitation to Pay Additional Fees, Application No. PCT/US2004/035751, European Patent Office as International Searching Authority mailed May 12, 2010 (3 pages).
Narjes et al., "α-Ketoacids are Potent Slow Binding Inhibitors of the Hepatitis C Virus NS3 Protease," *Biochemistry*, 39:1849-1861 (2000).
Partial International Search Report (2 pages), PCT/US2004/035751, European Patent Office as International Searching Authority mailed May 12, 2010.
Pegg et al., "Slow-Binding Inhibition of Sialidase from Influenza Virus," *Biochemistry and Molecular Biology International*, 32(5):851-858 (Apr. 1994).
Perni et al., "Preclinical Profile of VX-950, a Potent, Selective, and Orally Bioavailable Inhibitor of Hepatitis C Virus NS3-4A Serine Protease," *Antimicrobial Agents and Chemotherapy*, 50(3):899-909 (Mar. 2006).
Motakis et al., "A Tight-Binding Mode of Inhibition is Essential for Anti-Human Immunodeficiency Virus Type 1 Virucidal Activity of Nonnucleoside Reverse Transcriptase Inhibitors," *Antimicrobial Agents and Chemotherapy*, 46(6):1851-1856 (Jun. 2002).

\* cited by examiner

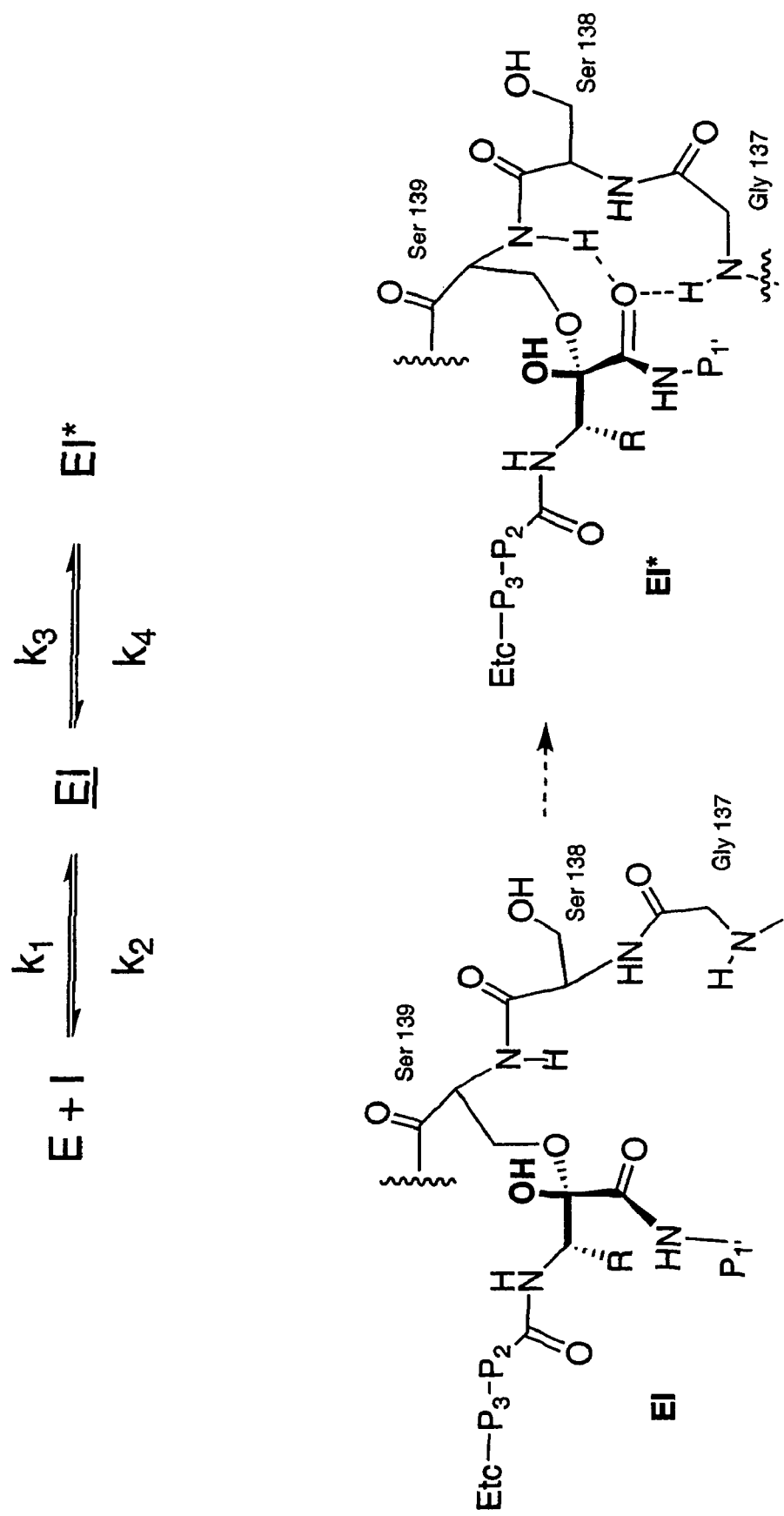

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence -continued

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: Modified with Abu-Psi-[COO]
<220> FEATURE:
<221> NAME/KEY: MOD_RES
<222> LOCATION: (8)..(8)
<223> OTHER INFORMATION: Modified with Dabcyl

<400> SEQUENCE: 1

Glu Asp Glu Asp Asp Ala Ser Lys
1               5
```

DRUG DISCOVERY METHOD

BACKGROUND

The present application claims the benefit of priority of U.S. Provisional Application No. 60/515,009 filed Oct. 27, 2003; and U.S. Provisional Application No. 60/526,346 filed Dec. 1, 2003. The entire text of each of the foregoing applications is specifically incorporated herein by reference in its entirety.

FIELD OF THE INVENTION

The present invention relates to methods of identifying compounds that inhibit infective agents.

BACKGROUND OF THE RELATED ART

As noted by Morrison and Walsh (1988), enzyme inhibitors can be categorized based on potency, reversibility, and rates of inhibitor interaction. Classical reversible, and non-time dependent inhibitors exhibit fast steps for binding and release from the enzyme. Equilibria for classical inhibitors are established quickly. For example, a classical inhibitor with a Ki value in the nanomolar range may have rates of binding of $10^6$-$10^8$ $M^{-1}sec^{-1}$ and rates of release from enzyme-inhibitor complex at 1-100 $sec^{-1}$. In contrast, slow binding inhibitors show a slow time-dependent onset of inhibition. The establishment of equilibria among the enzyme, inhibitor and enzyme-inhibitor complexes occurs in seconds to minutes. A tightened enzyme-inhibitor complex is slowly formed in one or two steps. The onset of binding (on-rates) may be fast or slow for these inhibitors, but slow off-rates (release from the enzyme inhibitor complex), in the order of seconds to minutes to hours, dominate for slow binding inhibitors. The three mechanisms, one for classical inhibition and two models for slow binding inhibition are illustrated below:

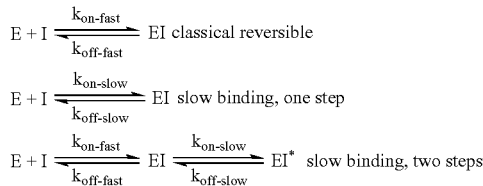

Both the slow binding mechanisms are highlighted by the slow rate of release of inhibitor from the enzyme-inhibitor complex. The two step mechanism is often considered a prototype of slow binding inhibition which assumes rapid formation of an enzyme-inhibitor complex which then slowly isomerizes to a tightened complex, EI*. Release of inhibitor from the enzyme-inhibitor complex of either the one step or two step mechanism is exceedingly slow. (Sculley, Morrison and Cleland, 1996). These slow off rates often confer a high degree of potency to this type of inhibitor.

The need for improved antimicrobial agents, including antiviral agents is well known. Viral infections cause compelling human medical problems.

HCV is recognized as the causative agent for most cases of non-A, non-B hepatitis, with an estimated human sero-prevalence of 3% globally [A. Alberti et al., "Natural History of Hepatitis C," *J. Hepatology*, 31, (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31, (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et. al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et. al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et. al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et. al., "Expression and Identification of Hepatitis C Virus Polyprotein Cleavage Products," *J. Virol.*, 67, pp. 1385-1395 (1993); L. Tomei et. al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Several potential HCV protease inhibitors have been described in the prior art [PCT publication Nos. WO 02/18369, WO 02/08244, WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., *Bioorg. Med. Chem. Lett.*, 8, pp. 1713-18 (1998); W. Han et al., *Bioorg. Med. Chem. Lett.*, 10, 711-13 (2000); R. Dunsdon et al., *Bioorg. Med. Chem. Lett.*, 10, pp. 1571-79 (2000); M. Llinas-Brunet et al., *Bioorg. Med. Chem. Lett.*, 10, pp. 2267-70 (2000); and S. LaPlante et al., *Bioorg. Med. Chem. Lett.*, 10, pp. 2271-74 (2000)].

Nevertheless, the current understanding of HCV has not led to any other satisfactory anti-HCV agents or treatments. The only established therapy for HCV disease is interferon treatment. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277. (1989)] and induce long term remission in only a fraction (~25%) of cases [O. Weiland, "Interferon Therapy in Chronic Hepatitis C Virus Infection", *FEMS Microbiol. Rev.*, 14, pp. 279-288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

This invention addresses the above problems by providing novel drug discovery methods and compounds identified by those methods.

Presently, it takes between three and five years to bring new potentially therapeutic compounds from the early discovery to preclinical development (in vivo animal testing). This lead time requires a tremendous commitment of company resources. Understandably, a technique that could predict the efficacy of the multitude compounds that arrive at or near the initial synthesis stage of drug discovery would have an enormous impact on the efficiency with which new drugs are identified by eliminating, early in the drug discovery process, compounds that have an unfavorable efficacy profile. An immediate expected benefit of more powerful, early stage in vitro effcicacy testing is the reduction of the number of these three to five year drug discovery cycles that result in failures, and thus reduce the average number of cycles required to develop successful new therapeutics. Related benefits include reduced costs for drug development and more rapid availability of new pharmaceuticals to the medical community.

The present invention provides methods for prioritizing new chemical entities within a class for further development or for identifying such compounds as appropriate lead compounds that will be effective as therapeutic agents early in the drug development and discovery process. As such, these methods can be used to prioritize large numbers of new compounds for further drug development. In addition, the methods greatly increase the probability that an identified agent will be successful in preclinical efficacy testing. The adaptability of these in vitro methods for high-throughput analysis makes them an economical and cost-effective addition to a drug discovery program. In particular, the present invention relates to the kinetics of inhibitors of infectious agents and is directed to a drug discovery method comprising comparing a time a reversible inhibitor is bound to a target of an infectious agent; and a replication time of an infectious agent, or a life-cycle time of the infectious agent. Using such determinations, the present invention teaches methods for selecting a compound having activity against an infectious agent, comprising selecting a target in the agent; identifying a compound that binds reversibly with the target; determining the half life of the compound on the target; determining the half life of the replication cycle of the infectious agent; and selecting a compound that has a half life on the target of at least about 25% of the time of an average life cycle for the infectious agent.

Other embodiments are directed to methods of selecting a compound having activity against an infectious agent, comprising selecting a target in the agent; identifying a compound that binds reversibly with the target; determining the half life of the compound on the target; determining the half life of the replication cycle of the infectious agent; and selecting a compound that has a half life on the target of at least about 25% of the half life of the replication cycle of the infectious agent.

In still further embodiments, the selection methods described herein are directed to selecting a compound having activity against an infectious agent, comprising selecting a target in the agent; identifying a compound that binds reversibly with the target; determining the half life of the compound on the target; determining the half life of the replication cycle of the infectious agent; and selecting a compound that has a half life on the target of at least about 25% of the time of the target's turnover.

Typically, the may be about 25%, about 50%, about 75%, about 100%, about 125%, about 150%, about 175%, about 200%, about 225%, about 250%, about 275% to about 300%. These are merely exemplary percentages and other integers in between any of these numbers are contemplated to be determinable and encompassed by the parameters set forth herein.

The invention further is directed to a method for selecting a compound as an anti-infective agent against a target of the agent, wherein the half life of the compound bound to the target is from about 25% to about 300% of the half life of the infective agent, from about 25% to about 300% of the replication time of the infective agent, or from about 25% to about 300% of the half life of the target turnover.

The methods described herein comprise performing an in vitro measurement of compound koff or enzyme-compound (i.e., enzyme-inhibitor) complex half life. In further embodiments, the invention involves a demonstration of a delayed maximal response in a viral replication system or a replicon system. In some aspects of the invention, the methods involve measuring sustained effects in inhibitor wash-out studies using a cellular replicon or replication system.

The methods of the invention form an adjunct to drug discovery methods wherein the methods may involve performing a first determination of e.g., the half life on the target of the compound as compared to the time of an average life cycle for the infectious agent and a second method that determines the half-life vis a vis another parameter.

Additional embodiments are directed to methods of selecting a viral inhibitor, comprising demonstrating a delayed maximal response in a viral replication system or a replicon system. Other methods involve assaying compounds for activity against an infectious agent, comprising determining a) a time a reversible inhibitor is bound to a target of the infectious agent; and b) a replication time of the infectious agent.

In the methods of the invention, the infectious agent may be a virus having a fast replicating life cycle. An exemplary such virus is Hepatitis C virus. In specific embodiments, the target for the methods described herein is Hepatitis C virus NS3/4A protease.

Also encompassed by the invention are compounds selected by methods described herein. In specific embodiments, the compound is an analog or derivative of VX-950. Such compound may be formulated into suitable compositions that further comprise a pharmaceutically acceptable salt, derivative or prodrug thereof in an amount effective to inhibit a serine protease; and a acceptable carrier, adjuvant or vehicle. Preferably, the compositions are formulated for administration to a patient. The compositions may further comprise an additional agent selected from an immunomodulatory agent; an antiviral agent; a second inhibitor of HCV protease; an inhibitor of another target in the HCV life cycle; a cytochrome P-450 inhibitor; or combinations thereof. Such additional agents include but are not limited to immunomodulatory agents such as $\alpha$, $\beta$, or $\gamma$-interferon or thymosin; antiviral agents such as ribavirin, amantadine, or thymosin; inhibitor of another target in the HCV life cycle such as an inhibitor of HCV helicase, polymerase, or metalloprotease. Preferably, the cytochrome P-450 inhibitor is ritonavir.

The compound identified herein may be used in methods of inhibiting the activity of a serine protease comprising the step of contacting said serine protease with such a compound. The serine protease is preferably an HCV NS3 protease.

The compositions identified herein may be used in methods of treating an HCV infection in a patient. Such methods may advantageously take advantage of the additional step of administering to said patient an additional agent selected from an immunomodulatory agent; an antiviral agent; a second inhibitor of HCV protease; an inhibitor of another target in the HCV life cycle; or combinations thereof; wherein said additional agent is administered to said patient as part of a combined composition or as a separate dosage form.

Also contemplated are methods of eliminating or reducing HCV contamination of a biological sample or medical or laboratory equipment, comprising the step of contacting said biological sample or medical or laboratory equipment with a composition identified using the methods described herein. Fro example, the sample or equipment is selected from blood, other body fluids, biological tissue, a surgical instrument, a surgical garment, a laboratory instrument, a laboratory garment, a blood or other body fluid collection apparatus; a blood or other bodily fluid storage material.

Additionally, there are provided methods of testing the ability of a compound to inhibit Hepatitis C virus activity, comprising contacting the compound with HCV replicon cells for at least 3 days; and evaluating inhibition of HCV. Preferably, the HCV inhibition is evaluated by determining (or estimating) the reduction of HCV RNA in the cells. In other embodiments, the HCV inhibition is evaluated by determining (or estimating) a copy number of HCV replicon RNA per replicon cell. Preferably the HCV replicon cells are at a low density. In specific embodiments, the compound and the HCV replicon cells are contacted for at least 5 days.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 1 depicts an enzyme-inhibitor complex in accordance with this invention.

DESCRIPTION OF THE PREFERRED EMBODIMENTS

This invention provides methods for assaying compounds for activity as antimicrobial agents.

Applicants developed these methods in comparing certain slow binding inhibitors and classical inhibitors of HCV NS3. Some activated carbonyl species exhibit slow-binding inhibition against serine and cysteine proteases. These species include, among others, diketones, and ketoamides. A ketoamide inhibitor of HCV protease demonstrated slow binding inhibition against the enzyme, and depending on the molecule, fit either one-step or two-step mechanisms of slow binding inhibition. Regardless of mechanism, the ketoamides exhibit off rates (from NS3), which are on the order of $10^{-4}$ $sec^{-1}$. These translate into half-lives for the tightened complexes of 10 minutes to 6 hour. In certain preferred embodiments, the half-lives are between 30 minutes and 3 hours, more typically between 30 minutes and 1 hour.

Advantageously, this time on the target is a substantive portion of both the viral replication cycle and the viral life cycle. Applicants have found that if a compound stays on a microbial target for a significant part of that microbes replication or life cycle then the compound is a significantly better inhibitor than one with a relatively fast $K_{off}$.

Accordingly, one embodiment of this invention provides a method identifying anti-infective compounds by comparing a) the compound's time on the target and b) the lifetime of the microbe, the replication time of the microbe, or the turnover rate of the a specific target within the microbe. The time that a compound stays on a target relative to the life cycle, replication time, or target turnover time, may vary from compound to compound and target to target.

Applicants have discovered that compounds that bind to an inhibitor for a substantial portion of an infectious agent's life cycle (or other benchmark as disclosed herein), are particularly effective against the infectious agent.

A critical question in any drug discovery effort is which assay to use to select compounds for further testing and/or further development. Once an assay is selected and results obtained, a further critical question is how to use those results to select a compound of interest (e.g., one to investigate further; one that will be a successful drug). These uncertainties lead to problems in effectively and efficiently conducting drug discovery.

Applicants' invention addresses these problems by providing assays and a method of using the assays to conduct drug discovery. Furthermore, applicants' invention provides potent reversible inhibitors. Irreversible inhibitors sometimes have deleterious effects in vivo. Applicants' invention addresses this problem by providing inhibitors that are slow, yet reversible.

Many inhibitors spend relatively little time continuously bound to a target. Rather, they are rapidly associating with and then an disassociating from the target. Therefore, even if the overall (or cumulative) time that an inhibitor is bound to a target may be relatively high, the time the inhibitor is bound, each time that it binds, may be relatively low. During the time that an inhibitor is not bound to a target, essential steps in the agent's life cycle may occur unhindered. Therefore, even though the inhibitor may be bound to the target for significant portions of time, the infectious agent is still able to carry out essential functions (as the bound time is noncontiguous).

This invention may be practiced with any infectious agent, including any class of virus. In a specific embodiment, the invention is practiced with fast replicating life cycle viruses, especially with positive RNA viruses. This class of viruses does not include retroviruses or viruses with DNA intermediates. In a more specific embodiment, this invention may be practiced with Hepatitis C virus.

Applicants have identified the importance of certain measurements (or comparisons) in the drug discovery process. Traditional measurements, such as Ki and/or IC50, although useful, may not be sufficient for fully evaluating an inhibitor. Such measurements may, however, be used in conjunction with this invention.

An important aspect of this invention is the time an inhibitor remains associated with the target after each time it binds (as express by $K_{off}$ or $t_{1/2}$ of the target-inhibitor complex). In particular, applicants' invention provides that the time a compound remains associated with a target after each time that it binds to the target correlates with the effectiveness that the compound inhibits the target.

In one embodiment, this invention provides a selection criteria for drug discovery. Thus, the techniques described herein can be used to prioritize and identify compounds that will be of a potential therapeutic value. Method for identifying such compounds are therefore contemplated to be useful in the general prioritization and identification of compounds that will serve as lead therapeutic compounds for drug development. Steps involved in a method of this invention may optionally comprise:

Identifying an inhibitor or a subset of inhibitors to be evaluated in accordance with this invention.

Determining whether a compound of interest is reversible.

Determining the time the inhibitor is bound to a target (i.e., the time that it is bound after each time that it binds).

Determining the half life of an infectious agent.

Determining the replication cycle time of an infectious agent.

Determining the half life of a target in an infectious agent.

Selecting an inhibitor that is bound to the target for a significant portion of viral half, replication half life, or target half life.

In the present invention, it is determined that the inhibitors that are most effective in producing a positive effect are reversible, they covalently bind the target, their binding is tight and slow-binding. These parameters may be calculated using routine techniques. VX-950 is one such inhibitor and it binds its target at an IC50 of 350 nm a CC50 83 μM. The half-life of the bound complex is relatively long as compared to the half life of the infection agent within the human (e.g., VX-950 reversible, covalently and slowly has a tight binding with the protease of HCV, where the complex has a $t_{1/2}$ of 1 hour whereas the HCV has a $t_{1/2}$ in the human of approx. 3 hours).

In one embodiment, this invention provides a viral clearance assay. This assay is an extension of previous assay methods. Applicants' invention provides assays that are conducted for relatively long periods of time (e.g., 2 days or longer). These assays allow for determining the amount of drug needed obtain viral clearance (i.e., to reduce a viral load to about zero) and to determine whether rebound occurs. These assays would be valuable in predicting efficacy in animal models and in predicting efficacy in humans. It emphasizes measuring a sustained response over an initial response.

Accordingly, also provided by this invention, is a method for doing a replicon (or similar assay) for greater than about 2 days. Applicants have found that such an assay is particularly useful in drug discovery, (for, e.g., selecting and characterizing inhibitors). In a more specific embodiment, the assay is done for about 9 days or more. The specific number of days may vary (e.g., any minimum number of days over about 2 days). However, most embodiments of this invention will use longer assay times than about 2 days. Such embodiments include times of about 9 days to about 27 days. More specific embodiments include a minimum number of days of about 6, 7, 8, 9, 10, 11, or 12 days and a maximum number of days of about 24, 25, 26, 27, 28, 29, or 30 days.

One embodiment provides contacting a compound and a HCV replicon cell for at least about 3 days. Other embodiments provide contacting for at least about 3, 4, 5, 6, 7, 8, or 9 days.

Determining includes measuring or obtaining from other sources (e.g., publications), etc. As would be recognized by skilled practitioners there are various ways to obtain the times and/or half life values that are called for by this invention. Viral half life values are typically measured. In practicing this invention, such half life numbers may be determined by known methods or otherwise obtained (e.g., from the literature; see, e.g., A. S. Perelson et al., "HIV-1 Dynamics in Vivo: Virion Clearance Rate, Infected Cell Life-Span, and Viral Generation Time" *Science* 1996 Mar. 15; 271: 1582-1586; M. A. Novak, "Viral dynamics in hepatitis B virus infection" PNAS 1996; 93: 4398-4402; A. U. Neumann et al. "Hepatitis C Viral Dynamics in Vivo and the Antiviral Efficacy of Interferon-α Therapy" Science, 282 pp. 103-107 (1998); and B. Roizman and P. Palese, "Multiplication of Viruses: An Overview" in Fields Virology, Third Ed., pp. 101-11 (1996). Half life values of viral replication as usually inferred experimentally (by, for example, measuring radioactive incorporation). Viral half life values are readily available.

Advantageously, practicing this invention using the half-life of an infectious agent as the reference point would, necessarily, encompass both the viral replication half life and the target turnover half life (as the viral replication half life and the target turnover half life are both less than the viral half life).

"Substantive portion" as used herein refers to about 1% or more. A specific upper limit would be about 200% or about 300%. Other specific embodiments of this invention include lower limits of about 10%, about 25%, about 33% about 50% and about 75% (including any integers therein). Other specific embodiments include upper limits of about 150%, 125%, 100%, 75% and 50% (including any integers therein). In the case of Hepatitis C virus NS3/4A protease a preferred substantive portion is about 33% to about 50%.

It should be understood the advantages of this invention may be realized with different substantive portions depending on the corresponding viral measurement. For example, the appropriate time for a compound to be bound to a target may be less if the relevant measurement is of replication cycle time, and even less if the relevant measurement is target turnover time (as target turnover time is less than replication time, which is less than the time of viral life).

Although an example provided herein involves a two-step binding mechanism, it is not essential to this invention that the mechanism is two-step.

In another embodiment this invention provides kits for conducting the assays and methods of this invention. Typically, such a kit will comprise, e.g. reagents or other materials (in appropriate containers) for conducting the assay and written instructions for conducting the assay.

This invention also provides a compound identified or selected according to this invention.

Another embodiment of this invention provides a composition comprising a compound selected according to this invention or a pharmaceutically acceptable salt thereof. According to a preferred embodiment, the compound of Formula A is present in an amount effective to decrease the viral load in a sample or in a patient, wherein said virus encodes a serine protease necessary for the viral life cycle, and a pharmaceutically acceptable carrier.

In particular embodiments, the structure of the starting compound has a structure of VX-950 (shown below in Formula B). Although VX-950 is exemplified, any stereoisomer of 950 could be used, with mixtures of the D- and L-isomers at the n-propyl side chain being expressly included. The following structure, Formula A depicts such diastereoisomer. This is a mixture of compounds of Formula B (VX-950) and Formula C.

Formula A

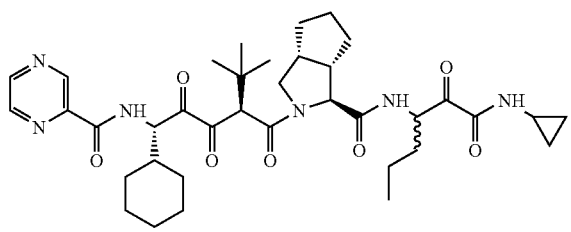

Formula B

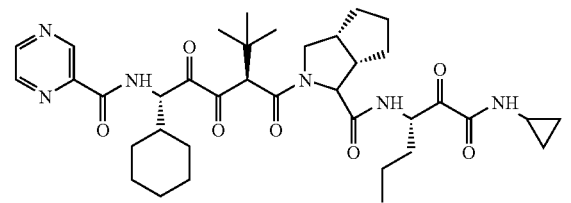

Formula C

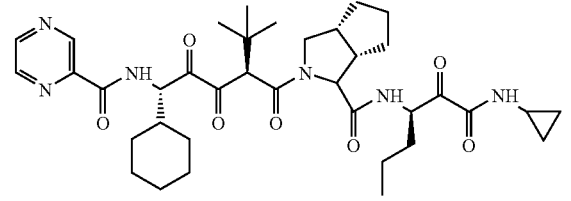

It is contemplated that additional agents that are related to or derivative of Formula A may be identified through rational drug design and tested for their efficacy using the methods described herein. Once useful compounds are thus identified, the compounds are prepared as useful formulations for treatment of disorders. Rational drug design may be used to serially modify different positions on this molecule to produce derivatives thereof that may be useful as protease inhibitors. Methods are known for developing models from crystal structure by, for example, computer-implemented methods molecular modeling proteases such as HCV NS3/4A protease have previously been described, e.g., in U.S. Pat. No. 6,162,613, WO 98/11134, and/or WO 02/068933. As is recognized in the art, a protein may be crystallized in the presence of the absence of a ligand (such as a compound being evaluated). Such crystallization studies may readily be performed with derivatives elucidated through rational drug design to identify agents that have a binding capacity and/or therapeutic efficacy. Such compounds may then be tested according to the methods of the present invention which will allow the elucidation of more effective therapeutic agents that are able to reversibly bind the target more tightly, in a covalent binding using a slow-binding mechanism.

The methods may involve use of a cell culture, which may be a primary cell in culture or it may be a cell line. The cells may be obtained from any mammalian source that is amenable to primary culture and/or adaptation into cell lines. In lieu of generating cell lines from animals, such cell lines may be obtained from, for example, American Type Culture Collection, (ATCC, Rockville, Md.), or any other Budapest treaty or other biological depository. The cells used in the assays may be from an animal source or may be recombinant cells tailored to express a particular characteristic of, for example, a particular disorder for which the drug development is being considered. Preferably, the cells are derived from tissue obtained from humans or other primates, rats, mice, rabbits, sheep and the like. Techniques employed in mammalian primary cell culture and cell line cultures are well known to those of skill in that art. Indeed, in the case of commercially available cell lines, such cell lines are generally sold accompanied by specific directions of growth, media and conditions that are preferred for that given cell line.

In particular embodiments, the assays may be performed in multiwell (e.g., 96-well) plates.

Various concentrations of the test compound being tested are added to the target, or the virus. Furthermore, the target may be exposed to the test compound at any given phase in the growth cycle of the virus. For example, in some embodiments, it may be desirable to contact the virus particles with the compound at the same time as a viral growth is initiated. Alternatively, it may be preferable to add the compound at a later stage in the viral life-cycle. Determining the particular stages of the virus life cycle are in is achieved through methods well known to those of skill in the art.

The varying concentrations of the given test compound are selected with the goal of including some concentrations at which no toxic effect is observed and also at least two or more higher concentrations at which a toxic effect is observed. A further consideration is to run the assays at concentrations of a compound that can be achieved in vivo. For example, assaying several concentrations within the range from 0 micromolar to about 300 micromolar is commonly useful to achieve these goals. It will be possible or even desirable to conduct certain of these assays at concentrations higher than 300 micromolar, such as, for example, 350 micromolar, 400 micromolar, 450 micromolar, 500 micromolar, 600 micromolar, 700 micromolar, 800 micromolar, 900 micromolar, or even at millimolar concentrations. The estimated therapeutically effective concentration of a compound provides initial guidance as to upper ranges of concentrations to test.

In an exemplary set of assays, the test compound concentration range under which the assay is conducted comprises dosing solutions which yield final test compound assay concentrations of 0.05 micromolar, 0.1 micromolar, 1.0 micromolar, 5.0 micromolar, 10.0 micromolar, 20.0 micromolar, 50.0 micromolar, 100 micromolar, and 300 micromolar of the compound in assay medium. As mentioned, these are exemplary ranges and it is envisioned that any given assay will be run in at least four different concentrations, more preferably the concentration dosing will comprise, for example, 4, 5, 6, 7, 8, 9, 10, 11, 12, 13, 14, 15 or more concentrations of the compound being tested. Such concentrations may yield, for example, a media concentration of 0.05 micromolar, 0.1 micromolar, 0.5 micromolar, 1.0 micromolar, 2.0 micromolar, 3.0 micromolar, 4.0 micromolar, 5.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 55.0 micromolar, 60.0 micromolar, 65.0 micromolar, 70.0 micromolar, 75.0 micromolar, 80.0 micromolar, 85.0 micromolar, 90.0 micromolar, 95.0 micromolar, 100 micromolar, 110.0 micromolar, 120.0 micromolar, 130.0 micromolar, 140.0 micromolar, 150.0 micromolar, 160.0 micromolar, 170.0 micromolar, 180.0 micromolar, 190.0 micromolar, 200.0 micromolar, 210.0 micromolar, 220.0 micromolar, 230.0 micromolar, 240.0 micromolar, 250.0 micromolar, 260.0 micromolar, 270.0 micromolar, 280.0 micromolar, 290.0 micromolar, and 300 micromolar in the test composition.

The compounds to be tested may include fragments or parts of naturally-occurring compounds or may be derived from previously known compounds through a rational drug design scheme. It is proposed that compounds isolated from natural sources, such as animals, bacteria, fungi, plant sources, including leaves and bark, and marine samples may be assayed as candidates for the presence of potentially useful pharmaceutical compounds. Alternatively, pharmaceutical compounds to be screened for toxicity could also be synthesized (i.e., man-made compounds).

The types of compounds being monitored may be antiviral compounds, antibiotics, anti-inflammatory compounds, antidepressants, analgesics, antihistamines, diuretic, antihypertensive compounds, antiarrythmia drugs, chemotherapeutic compounds for the treatment of cancer, antimicrobial compounds, among others.

Regardless of the source or type of the compound to be tested for cytotoxicity, it may be necessary to monitor the biological activity of the compounds to provide an indication of the therapeutic efficacy of a particular compound or group of compounds. Of course, such assays will depend on the particular therapeutic indication being tested. Exemplary indications include HCV or other viral infection.

In preferred embodiments, the assays of the present invention may be used as part of a drug discovery program to identify a putative therapeutic compound with increased efficacy against such disorders. Drug discovery begins with the identification of a range of candidate substances that show promise in a targeted therapeutic area. This first step can result in several hundred "hits". The discovery team is then faced with the question of which compounds to run in subsequent screens. The selection methods of the invention performed at this stage in drug discovery would allow prioritization of the compounds based on estimated efficacy due to the nature and the degree of binding of the test compound to the target. The top compounds are then subjected to further screens for efficacy and specificity. In the present invention an exemplary core or template structure such as VX-950 may be used for future drug development efforts. Other structures may likewise provide useful. Once the template is selected, additional chemistry and structure activity analyses are performed to increase the potency of the compound. This process yields the lead compounds. A screen using the methods of the invention at this stage of the process may be performed to provide efficicacy data on these potential lead compounds.

The top lead compounds are selected to enter preclinical animal testing. Incorporation of the present selection methods early in the discovery process should greatly reduce the number of compounds that fail during this late stage.

The screening technique described in the present invention may be employed at any stage in the drug discovery program but may prove especially valuable early in the discovery process. The information obtained from such analysis provides the chemists with the appropriate information to maximizing potency and efficacy in the new templates. Using these methods, the putative therapeutic compounds can be ranked or prioritized based on their relative binding efficacies and compared to known drugs in the same therapeutic and chemical class. For example, the VX-950 could be used as a reference compound for new anti-HCV agents.

High throughput assays for screening numerous compounds for efficacy using the methods of the invention are specifically contemplated. In certain embodiments, the high throughput screens may be automated. In high throughput screening assays, groups of compounds are exposed to a biological target. These groups may be assembled from collections of compounds previously individually prepared and since stored in a compound bank, the assembly being random or guided by the use of similarity programs from which similar structures are formed.

In addition, there has also been a rapid growth in the deliberate preparation and use of libraries and/or arrays of compounds. Each library contains a large number of compounds which are screened against a biological target such as an enzyme or a receptor. When a biological hit is found, the compound responsible for the hit is identified. Such a compound, or lead, generally exhibits relatively weak activity in the screen but forms the basis for the conduct of a more traditional medicinal chemistry program to enhance activity. The libraries may be prepared using the rapidly developing techniques of combinatorial chemistry or by parallel synthesis (DeWitt et al, *Proc Natl Acad Sci,* 90, 6909, 1993; Jung et al, *Angew Chem Int Ed Engl,* 31:367-83, 1992; Pavia et al., *Bioorg Med Chem Lett,* 3:387-96, 1993).

Alternatively, the compounds to be screened may be from a library based upon a common template or core structure such as e.g., the VX-950 structure described above. Scuh techniques are described in e.g., WO 95/32184 (oxazolone and aminidine template), WO 95/30642 (dihydrobenzopyran template) and WO 95/35278 (pyrrolidine template). The template will have a number of functional sites, for instance three, each of which can be reacted, in a step-wise fashion, with a number of different reagents, for instance five, to introduce 5×5×5 different combinations of substituents, giving a library containing 125 components. The library will normally contain all or substantially all possible permutations of the substituents. The template may be a 'biased' template, for instance incorporating a known pharmacophore such as a benzodiazepine ring or an 'unbiased' template, the choice of which is influenced more by chemical than biological considerations.

Thus, the present invention may be used to identify lead compounds for drug discovery. In addition to the library screening discussed above, such lead compounds may be generated by random cross screening of single synthetic compounds made individually in the laboratory or by screening extracts obtained from natural product sources such as microbial metabolites, marine sponges and plants.

In another alternative, the compounds may be generated through rational drug design based on the structure of known biologically active compounds and/or their sites of biological action. This has now been complemented by the powerful techniques of computer-assisted drug design. The goal of rational drug design is to produce structural analogs of biologically active molecules of interest. Such technologies will yield potentially thousands of compounds for a particular indication that may be screened for cytotoxicity using the present invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2 hydroxyethanesulfonate, lactate, maleate, methanesulfonate, 2 naphthalenesulfonate, nicotinate, oxalate, pamoate, pectinate, persulfate, 3 phenyl propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N methyl D glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I, and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In another embodiment, the compositions of this invention additionally comprise another anti-viral agent, preferably an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2—NS3 inhibitors and NS3—NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments; laboratory instruments and garments; blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In certain aspects of the present invention, all the necessary components for conducting the selection and screening assays may be packaged into a kit. Specifically, the present invention provides a kit for use in such an assay comprising a packaged set of reagents for conducting the assay as well as test or reference compounds, instructions packaged with the reagents for performing one or more variations of the assay of the invention using the reagents. The instructions may be fixed in any tangible medium, such as printed paper, or a computer-readable magnetic or optical medium, or instructions to reference a remote computer data source such as a world wide web page accessible via the internet.

Although certain exemplary embodiments are depicted and described below, it will be appreciated that practice of this invention can be according to the methods described generally above and/or generally available to one of ordinary skill in the art.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The rates of onset of slow binding inhibition were determined by a modification of the method for measurement of progress curves described in Narjes et. al. (2000).

Enzyme activity was measured using a continuous assay which monitored the increase of fluorescence which resulted from cleavage of the internally quenched fluorogenic depsipeptide (FRET substrate):

Ac-Glu-Asp-Glu-(Edans)-Asp-Asp-Aminobutyrl-ψ [COO]-Ala-Ser-Lys -(Dabcyl)-NH2 (SEQ ID NO: 1)
In the Sequence Listing Please introduce the computer-readable form of the Sequence Listing (filename: 40506_SeqListing.txt) submitted herewith as part of the application as filed.

Two hundred nanomolar NS3 (protease domain) was pre-incubated for 10-15 minutes at room temperature in 50 mM HEPES, pH 7.5, 25 µM KK4A and 5 mM dithiothreitol (DTT). An aliquot of this mixture was then added to 50 mM HEPES, pH 7.5, 15% v/v glycerol, 25 µM KK4A and 5 mM dithiothreitol containing 4 µM to 8 µM FRET peptide substrate (4-8×Km) and inhibitor dissolved in DMSO or DMSO alone as control (1% v/v final concentration; the total assay volume was 1.0 mL and the final enzyme concentration was 1.0 nM. The increase in fluorescence (excitation wavelength, 350 nm; emission wavelength, 490 nm) was monitored in a quartz cuvette thermostated at 30 C using a circulating water bath, in a Perkin-Elmer LS-50B spectrofluorimeter. Activity was monitored for 2-3 hours.

Progress curves for inhibition resulting from these experiments were fitted to the following equation:

$$F_{(t)}=v_s(t)+(v_o-v_s)(1-\exp(-k_{obs}*t))/k_{obs}+C \quad (1)$$

In which $F_{(t)}$ is the fluorescence at time, t, $v_s$ is the final steady state velocity, $v_o$ is the initial velocity in the absence of inhibitor at t=0, $k_{obs}$ is the first-order rate constant for the approach to steady state, and C is the initial displacement of $F_{(t)}$ at t=0.

Values of $k_{obs}$ are determined at increasing inhibitor concentrations and fitted to either of the following equations:

$$Y=k_{off}+(k_{on}*I/Ki)/(1+S/Km+I/Ki) \quad (2)$$

$$Y=k_{off}+k_{on}*I/(1+S/Km) \quad (3)$$

In which $k_{on}$ is the rate of onset for inhibition and $k_{off}$ is the rate of release from the tightened enzyme inhibitor complex I is the inhibitor concentration, S is substrate concentration, Km is the substrate Michaelis constant, and Ki is the inhibition constant for the initial enzyme-inhibitor complex which is formed prior to the slowly formed tightened complex. (Sculley, Morrison and Cleland, 1996).

Although the $k_{off}$ is calculated in using the equations above, the value was determined experimentally as follows.

The tightened enzyme-inhibitor complex was formed by preincubation of 200 nM NS3 with 1 µM inhibitor in DMSO (final DMSO at 0.4% v/v) in a buffer mix containing 25 µM KK4A, 50 mM HEPES, pH 7.5, 15% v/v glycerol, and 5 mM DTT for 2 hours at 30 C. After the 2 hour incubation, the complex was diluted 200-fold into the same buffer mix, but with 12.5 µM to 25 µM FRET substrate (12.5-25×Km). Recovery of activity was monitored in a cuvette as described above for 3 hours. Under these conditions. The data this generated were fitted to equation 1. Under these conditions, reassociation of inhibitor with enzyme is negligible, and $k_{obs}=k_{off}$.

Half-lives of activity recovery were determined using the following equation:

$$T_{1/2}=0.693/k_{off} \quad (4)$$

Results

The $k_3$, $k_4$ (on- and off-rates, respectively, determined as described above) for two representative compounds are shown in the table below. The Ki values which reflect the formation of the initial complex, were determined separately using the two different assay conditions: 1, above except the concentration of FRET substrate was 1 µM=Km, or 2), determined using an HPLC based assay which was a modification of that described in Landro et. al, 1997. Enzyme activity was measured by separation of substrate and products using a reversed phase HPLC microbore column (Phenomenex Jupiter C18, 5 µm, 150×2 mm; column heated to 40C; 5%-60% acetonitrile with 0.1% trifluoroacetic acid as the counterion at 4.6% per minute) and a Hewlett-Packard 1100 system with autoinjection, themostatted column chamber, and a diode array detection at 210 and 280 nm. Ki values were calculated from rate vs. inhibitor concentration by non-linear least square fitting to the tight binding inhibition equation (Morrison, 1969) using Prism software (GraphPad).

VX-950 appears to follow a mechanism which is likely a hybrid of the one-step and two-step mechanisms. This likely arises due to differences among the rate constants for formation of the initial complex and the tightened complex, hence a range of values is given for the Ki of the tightened complex. However, the off-rate, $k_4$, is determined experimentally and is the same regardless of the one or two step model.

| | VX-950 |
|---|---|
| $k_3$ (sec$^{-1}$) | 0.003-0.02 |
| $k_4$ (sec$^{-1}$) | 0.0002 |
| Ki | 45-190 nM |
| Ki* | 1-10 nM |
| $t_{1/2}$ (min) | 58 |

This compound exhibits slow release of inhibitor from the tightened enzyme-inhibitor complex, and has a long half-life for recovery of activity.

Example 2

2-Day HCV Replicon Assay

Cells containing subgenomic HCV RNA (replicon) are maintained in DMEM containing 10% fetal bovine serum (FBS), 0.25 mg/ml of G418. On the day prior to the assay, $10^4$ HCV replicon cells were plated in each well of a 96-well plate in the presence of 10% FBS but no G418 to allow the cells to attach and to grow overnight (~16 h). On the day of the assay, the culture media were removed and replaced with media with serially diluted compounds in the presence of 2% FBS and 0.5% DMSO. The replicon cells were treated with the compound for 48 hours, then the reduction of HCV RNA in the cells was determined by quantitative RT-PCR (Taqman) and the cytotoxicity of the compound was determined by MTS-based cell viability assay. The $IC_{50}$ and $CC_{50}$ of the compound were calculated from these assays using 4-parameter curve fitting. $IC_{50}$ represents the concentration of the compound at which the HCV RNA level in the replicon cells is reduced by 50%. $CC_{50}$ represents the concentration of the compound at which the cell viability is reduced by 50%.

Example 3

9-Day Viral Clearance (VC) Assay

The replicon cells were plated at a very low density (500 cells per well) in a 96-well plate so that they won't reach confluence after 9 days in culture. Compounds were serially diluted to concentrations at multiples (2×, 5×, etc.) of their respective IC50's in media containing 10% FBS and 0.2% DMSO. The media containing compounds were replaced every three days. The cells were treated with compounds for 3, 6 or 9 days. At the end of experiment, cell numbers were determined in an MTS-based assay with an established standard curve, the level of HCV RNA in the cells was measured by quantitative RT-PCR (Taqman), and then the copy number of HCV replicon RNA per cell in each sample was calculated.

Example 4

9~27-Day Viral Clearance/Rebound Study

On the day prior to the assay, $2\times10^5$ HCV replicon cells were plated in each well of a 6-well tissue culture plate. Compounds were serially diluted to concentrations at multiples (10×, 50×, etc.) of their respective IC50's in media containing 10% FBS and 0.2% DMSO. The HCV replicon cells were split to fresh media with compounds every three days before reaching confluence while a cell sample was taken at the same time. For the rebound experiment, the compounds were withdrawn after 13 days of treatment and G418 was added to the culture to enrich the remaining HCV replicon-positive cells. For each cell sample taken, the number of viable cells was determined by Guava ViaCount assay, the level of HCV RNA in the cells was measured by quantitative RT-PCR (Taqman), and then the copy number of HCV replicon RNA per cell in each sample was calculated.

Example 5

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit. 10,000 cells in 100 μl were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as "no compound" controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

Example 6

HCV Ki Assay Protocol HPLC Microbore Method for Separation of 5AB Substrate and Products Substrate:
NH2-Glu-Asp-Val-Val-(alpha)Abu-Cys-Ser-Met-Ser-Tyr-COOH A stock solution of 20 mM 5AB (or concentration of your choice) was made in DMSO w/0.2M DTT. This was stored in aliquots at −20 C.

Buffer: 50 mM HEPES, pH 7.8; 20% glycerol; 100 mM NaCl

Total assay volume was 100 μL

| | X1 (μL) | conc. in assay |
|---|---|---|
| Buffer | 86.5 | see above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30° C. for 5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5AB). This was incubated for 20 min at 30° C. The reaction was terminated by addition of 25 μL of 10% TFA. 120 μL aliquots were transferred to HPLC vials, and the SMSY product was separated from substrate and KK4A by the following method:

Microbore Separation Method:
    Instrumentation: Agilent 1100
    Degasser G1322A
    Binary pump G1312A
    Autosampler G1313A
    Column thermostated chamber G1316A
    Diode array detector G1315A
Column:
    Phenomenex Jupiter; 5 micron C18; 300 angstroms; 150×2 mm; P/O 00F-4053-B0
    Column thermostat: 40 C
    Injection volume: 100 μL
    Solvent A=HPLC grade water+0.1% TFA
    Solvent B=HPLC grade acetonitrile+0.1% TFA

| Time (min) | % B | Flow (ml/min) | Max press |
|---|---|---|---|
| 0 | 5 | 0.2 | 400 |
| 12 | 60 | 0.2 | 400 |
| 13 | 100 | 0.2 | 400 |
| 16 | 5 | 0.2 | 400 |
| 17 | 5 | 0.2 | 400 |

Stop time: 17 min
Post-run time: 10 min.

REFERENCES

Morrison J F, Walsh C T.(1988) "The behavior and significance of slow-binding enzyme inhibitors." Adv Enzymol Relat Areas Mol. Biol. 61:201-301.

Sculley, M J, Morrison, J F, Cleland, W W. (1996) "Slow-binding inhibition: the general case", Biochim. Biophys. Acta 1996; 1298 78-86.

Narjes F, Brunetti M, Colarusso S, Gerlach B, Koch U, Biasiol G, Fattori D, De Francesco R, Matassa V G, Steinkuhler C. (2000) "Alpha-ketoacids are potent slow binding inhibitors of the hepatitis C virus NS3 protease", Biochemistry 39, 1849-1861.

Landro, J. A., Raybuck, S. A., Luong, Y. P. C., O'Malley, E. T., Harbeson, S. L., Morgenstern, K. A., Rao, G., and Livingston, D. J. 1997, "Mechanistic role of an NS4A peptide co-factor with the truncated NS3 protease of hepatitis C virus: elucidation of the NS4A stimulatory effect via kinetic analysis and inhibitor mapping", Biochemistry, 36, 9340-9348.

Morrison, J. F. 1969, Biochim. Biophys Acta 185, 269-28.

Documents involving Hepatitis C inhibitors include, but are not limited to:

WO 03/087092, WO 03/006490, WO 03/064456, WO 03/064416, WO 03/035060, WO 02/060926, WO 02/079234, WO 02/48116, WO 02/48157, WO 00/31129, WO 02/18369, WO 02/08256, WO 02/08244, WO 02/08198, WO 02/08187, WO 01/81325, WO 01/77113, WO 01/74768, WO 01/64678, WO 01/07407, WO 00/59929, WO 00/09588, WO 00/09543, WO 99/64442, WO 99/50230, WO 99/38888, WO 99/07734, WO 99/07733, WO 98/46630, WO 98/46630, WO 98/22496, WO 98/17679, WO 97/43310, U.S. Pat. Nos. 6,018,020, 5,866,684, U.S. 20030008828, U.S. 20020177725, U.S. 20020016442, U.S. 20020016294, US60/500,670, or US60/488,591 (which as set forth below are hereby incorporated by reference).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

We claim:

1. A method for identifying a compound having activity against a Hepatitis C Virus (HCV), comprising:
   (a) contacting compounds with a target in the HCV;
   (b) determining whether or not said compounds bind reversibly with the target, wherein the target is an HCV enzyme selected from the group consisting of a protease, a helicase, and a polymerase;
   (c) measuring the half-life of compounds bound to the target; and
   (d) selecting a compound having activity against HCV based on the reversible binding property and on the half-life of compounds bound to the target, wherein a compound that binds reversibly to the target and has a half-life bound to the target of at least about 25% of the half-life of the replication cycle of HCV is identified as a compound having activity against HCV.

2. The method according to claim 1 wherein the method comprises
   an in vitro measurement of compound $K_{off}$ or target-compound (i.e., target-inhibitor) complex half-life.

3. The method according to claim 1, wherein the method further comprises a demonstration of a delayed maximal response in a viral replication system or a replicon system, wherein a compound that binds reversibly to the target, has a half-life bound to the target of at least about 25% of the half-life of the replication cycle of HCV, and has the delayed maximal response is identified as a compound having activity against HCV.

4. The method according to claim 1, wherein the method further comprises measuring sustained effects of the compound in inhibitor wash-out studies using acellular replicon or replication system, wherein a compound that binds reversibly to the target, has a half-life bound to the target of at least about 25% of the half-life of the replication cycle of HCV, and has sustained effects in inhibitor washout studies is identified as a compound having activity against HCV.

5. The method of claim 1, further comprising:
   demonstrating a delayed maximal response in a viral replication system or a replicon system, and
   measuring sustained effects of the compound in inhibitor wash-out studies using a cellular replicon or replication system,
   wherein a compound that binds reversibly to the target, has a half-life bound to the target of at least about 25% of the half-life of the replication cycle of HCV, has the delayed maximal response, and has sustained effects in inhibitor wash-out studies is identified as a compound having activity against HCV.

6. The method of claim 2, further comprising
   demonstrating a delayed maximal response in a viral replication system or a replicon system, and
   measuring sustained effects of the compound in inhibitor wash-out studies using a cellular replicon or replication system,
   wherein a compound that binds reversibly to the target, has a half-life bound to the target of at least about 25% of the half-life of the replication cycle of HCV, has the delayed maximal response, and has sustained effects in inhibitor wash-out studies is identified as a compound having activity against HCV.

7. The method according to claim 1, wherein the target is Hepatitis C virus NS3/4A protease.

8. A method for identifying a compound having activity against a Hepatitis C Virus (HCV), comprising:
   (a) contacting compounds with a target in the HCV, wherein the target is an HCV enzyme selected from the group consisting of a protease, a helicase, and a polymerase;
   (b) determining whether or not said compounds bind reversibly with the target;
   (c) measuring the half-life of the compounds bound to the target; and
   (d) selecting a compound having activity against HCV based on the reversible binding property and based on the half-life of compounds bound to the target, wherein a compound that has a half-life bound to the target of about 25% to about 300% of the half-life of the replication cycle of HCV is identified as a compound having activity against HCV.

9. A method for identifying a compound having activity against a Hepatitis C Virus (HCV), comprising:
   (a) contacting compounds with a target in the HCV, wherein the target is an HCV enzyme selected from the group consisting of a protease, a helicase, and a polymerase;
   (b) determining whether or not said compounds bind reversibly with the target;
   (c) measuring the half-life of the compounds bound to the target; and
   (d) selecting a compound having activity against HCV based on the reversible binding property and based on the half-life of compounds bound to the target, wherein a compound that has a half-life bound to the target of between 10 minutes and 6 hours is identified as a compound having activity against HCV.

10. The method of claim 9, wherein step (d) comprises selecting a compound having a half-life bound to the target of between 30 minutes and 3 hours.

11. The method of claim 9, wherein step (d) comprises selecting a compound having a half-life bound to the target of between 30 minutes and 1 hour.

12. The method according to any one of claims 8-10, wherein the method comprises an in vitro measurement of compound $K_{off}$ or target-compound (i.e., target-inhibitor) complex half-life.

13. The method according to any one of claims 8-10, wherein the method further comprises a demonstration of a delayed maximal response in a viral replication system or a replicon system, wherein a compound that binds reversibly to the target, has said half-life bound to the target, and has the delayed maximal response is identified as a compound having activity against HCV.

14. The method according to any one of claims 8-10, wherein the method further comprises measuring sustained effects of the compound in inhibitor wash-out studies using a cellular replicon or replication system, wherein a compound that binds reversibly to the target, has said half-life bound to the target, and has sustained effects in inhibitor washout studies is identified as a compound having activity against HCV.

15. The method according to any one of claims 8-10, wherein the target is Hepatitis C virus NS3/4A protease.

16. The method according to any one of claims 1, 8 and 9, further comprising measuring in vivo efficacy of the selected compound against HCV.

* * * * *